United States Patent [19]
Garbutt et al.

[11] Patent Number: 5,514,345
[45] Date of Patent: May 7, 1996

[54] METHOD AND APPARATUS FOR DISINFECTING AN ENCLOSED SPACE

[75] Inventors: Cornelius D. Garbutt, St. Augustine; Douglas A. Moxley, Ponte Vedra, both of Fla.

[73] Assignee: Ozact, Inc., Lake Worth, Fla.

[21] Appl. No.: 209,642

[22] Filed: Mar. 11, 1994

[51] Int. Cl.⁶ ........................ A61L 9/015
[52] U.S. Cl. .............. 422/124; 422/5; 422/186.07
[58] Field of Search .............. 422/4, 5, 29, 120, 422/123, 124, 186.07, 186.08, 186.14; 62/78, 264; 426/236

[56] References Cited

U.S. PATENT DOCUMENTS

| | | | |
|---|---|---|---|
| 3,576,593 | 4/1971 | Cicirello | 422/124 |
| 4,863,701 | 9/1989 | McMurray | 422/186.08 |
| 5,023,020 | 6/1991 | Machida et al. | 422/124 X |
| 5,069,880 | 12/1991 | Karlson | 422/186.19 |
| 5,116,574 | 5/1992 | Pearson | 422/28 X |
| 5,160,481 | 11/1992 | Weaver | 422/186.07 |
| 5,174,967 | 12/1992 | Fukuhara | 422/124 |
| 5,292,479 | 3/1994 | Haraga et al. | 422/124 X |
| 5,316,741 | 5/1994 | Sewell et al. | 422/186.07 X |

FOREIGN PATENT DOCUMENTS 3012245  1/1991  Japan ........................ 422/124

Primary Examiner—Robert J. Warden
Assistant Examiner—E. Leigh Dawson
Attorney, Agent, or Firm—Malin, Haley, DiMaggio & Crosby

[57] ABSTRACT

An apparatus for disinfecting an enclosed space for the preservation and sterilization of harvested foods, and for reducing toxic gas levels associated with confining animals in an enclosed space using ozone and an ozone distribution device.

3 Claims, 3 Drawing Sheets

METHOD AND APPARATUS FOR DISINFECTING AN ENCLOSED SPACE

BACKGROUND OF THE INVENTION

1. Field of the Invention

The present invention relates generally to a method and apparatus for disinfecting an enclosed space for the preservation and sterilization of harvested foods, vegetables, and flowers in a storage environment, and for reducing toxic gas levels associated with confining animals in an enclosed space, and more particularly to a method and apparatus for disinfecting an enclosed space by introducing a regulated ozone and oxygen gas mixture into the enclosed space.

2. Description of the Prior Art

One typical method for the preservation of harvested fruits, vegetables, and flowers on a large commercial scale is to store the product in an insulated room, or transport container such as an insulated trailer box with self-contained refrigeration (e.g. refrigerated trailer); a motor vehicle mounted insulated box with a self-contained or vehicle engine powered means of refrigeration; or with a detached insulated box with a self-contained means of refrigeration suitable for transport on a ship, barge, railroad car or over the road trailer (e.g. refrigerated cargo container) kept at low temperature, typically between 33° fahrenheit and 45° fahrenheit. In some of these refrigerated environments, the humidity may also be controlled, either by the removal or addition of moisture, to further preserve the appearance or freshness of the product. Some products, such as Vidalia sweet onions and all varieties of apples, can be kept in storage for longer periods than can be achieved by simple reduction in temperature. This longer term storage process is called controlled atmosphere storage and involves displacing of all but approximately 1% to 3% of the oxygen in the room with nitrogen and maintaining temperatures as close to freezing as can be achieved without actual freezing of the product.

These processes do extend the life of organic products such as vegetables, fruits, and flowers when compared to continued exposure of the fresh product to ambient temperatures. The principal purpose of the refrigerated room or transport container storage is to retard ripening by reducing the fresh products' generation of ethylene gas and to reduce the growth rate and product destroying abilities of opportunistic bacteria, fungus and molds. Because these storage and transport methods only retard and reduce natural processes, the term of storage is limited and variable depending on the temperature, humidity, and the population of plant pathogens contained in the storage and transport environment, as well as on the product itself.

The present invention provides an improved method and apparatus to enhance preservation and vegetable shelf life by sterilizing the ambient atmosphere in an enclosed space by introducing a regulated ozone and oxygen gas mixture into the enclosed space.

With respect to commercial food source animals, a typical method for housing animals on a large commercial scale in colder climates is to confine the animals to a building containing one or more rooms in which ventilation is controlled such that during the colder seasons there is not a lot of heat loss. Air exchange from outside to inside and vice versa is kept at a minimum to reduce energy consumption and to avoid chilling the animals, particularly the very young. Conversely, in hot climates, it necessary to cool the facility to avoid heat stressing the animals. Air exchange is reduced to a minimum to reduce energy costs for cooling. This reduction in the introduction of fresh air containing healthful levels of oxygen and some amounts of naturally occurring ozone is deleterious to the health of the animals. The lowered oxygen levels and the increase in toxic gases (ammonia, methane, and hydrogen sulphide being the principal gases) places a greater strain on the animals' kidneys due to the increased presence of toxins in the blood and is detrimental to the animals' respiratory system as elevated ammonia level is a mucus membrane irritant. Another affect of the reduced air exchange is a raising of the humidity level. Many fungus and bacteria are dormant at lower humidity levels and these become much more active as the relative humidity increases above 60%.

The present invention can continuously provide an oxygen and ozone injected treatment for the animal ambient air to improve energy efficiency while reducing toxins.

Thus the ozone and oxygen system of the present invention can be used for preserving the shelf life of produce such as vegetables and for improving the ambient air and energy efficiency for enclosed animals.

The present invention relates to a method and apparatus for treating ambient gases in an enclosed space with ozone and oxygen. During storage, the process of respiration of fruit is speeded up and so is ripening. Ethylene is produced which affects other fruit and so initiates even more intensive ripening. The external signs of this process are browning of the skin, softening of the flesh of the fruit and, finally, decay. Ozone gas ($O_3$), which is an allotrope of oxygen ($O_2$), can be used to extend the term of storage because it oxidizes the ethylene gas in the atmosphere of the storage environment and is lethal to bacteria, fungus, and molds. However, excessive concentrations of ozone can damage a product by oxidizing sugars and altering flavor, altering the metabolism of cut flowers thereby causing them to wilt, and accelerating other natural plant activity such as sprouting in bulb crops such as onions. Because there is no oxygen in a controlled atmosphere storage process, ozone must be manufactured from oxygen obtained from outside the storage environment. Ozone manufactured from ambient air, whether that contained within the storage room or introduced from outside, contains nitrous oxides and nitric acid that can affect flavor and cause discoloration of the product. Further damage can be caused to the storage room itself from acidic attack of the structural and operating components.

The introduction of a high purity oxygen and ozone mixture (e.g. 4%–7% $O_3$) into the storage environment significantly reduces ethylene gas levels by oxidation. Ethylene is broken down into water vapor and carbon dioxide. By maintaining a residual amount of ozone of 0.02 to 0.04 parts per million by weight in the air in the room after available ozone is consumed by reaction with the gases, the bacteria, fungus, and molds in the air and on surfaces are continuously suppressed. Additionally, this concentration of ozone is less than the 0.05 parts per million limit for human exposure in effect in Canada, Europe, and Japan, and the 0.1 parts per million limit in effect in the United States of America. This permits workers to move in an out of the ozonated area without hazard. Further, pathogens transported into the storage environment by humans are quickly suppressed.

Prior to the introduction of products into the storage or transport environment and in the absence of humans, the high purity oxygen and ozone mixture can be elevated to very much higher levels with no upper limit control in order to decontaminate and deodorize the storage or transport environment. This is particularly useful when the environment has been used to transport other products which may have rotted and released excessive levels of ethylene gas and plant pathogens. In other instances, such as the seasonal or the intermittent use of storage or transport, the refrigeration may have been interrupted and outside air introduced through openings. Bacteria, fungus, and mold colonies will have bloomed and will be at their peak. Furthermore, ozone eliminates or reduces mold build-up on cooling coils. Dirt and dust build-up is reduced, drastically reducing the number of times the cooling coils need cleaning and increasing energy efficiency. Some storage environments, particularly cargo containers, may have been previously used for refrigerated transport of other food stuffs, such as fish that leave a strong residual odor. As is well known, ozone is unmatched as a deodorizer. However, to totally eliminate "heavy" odors, higher concentrations (e.g. 0.1 p.p.m.) of ozone are required to react with gases in the air and odors trapped in materials. Ozone at a concentration of 0.1 p.p.m. will destroy microorganisms and eliminate most odors within 48 hours.

SUMMARY OF THE INVENTION

A method and apparatus for injecting and controlling the ambient gas in an enclosed space the purpose of which is to store fruits, vegetables or to house animals safely and efficiently.

The system employs the use of the enclosed space, a source of pure dry oxygen, an ozone generator, and a gaseous transport and transferring the ozone so generated into the desired enclosed space at desired levels for maintaining the ambient atmosphere in the enclosed space with desired levels of ozone and oxygen depending on the ultimate purpose of the enclosed space.

In one embodiment the oxygen source may be an oxygen generator that can generate dry pure oxygen in large quantities (e.g. five or ten liters) that has a fixed position relative to one or more rooms which are the enclosed spaces. A fluid control pipe thus is disseminated from the oxygen generating source to a plurality of ozone generators which are mounted either outside the enclosed space to be sterilized. The ozone generator also has a distribution device attached to its output such as an outlet pipe opening with or without a system of fans that allows for a predetermined amount of ozone to be distributed into each enclosed space as a function of time. Flow volume control is achieved by oxygen pressure to the ozone generator and internal metering within the ozone generator. Empirical calculations are made prior to the installation of the unit to achieve the proper amount of ozone and oxygen in a space based on the overall size of the space, the flow of gas, and the expected deterioration based on the commodities or produce in the enclosed space. Automated control of ozone amounts can be utilized in lieu of empirical calculations. If animals are in the space then separate considerations are made based on ventilation conditions and the like.

The system is also capable of being used with portable enclosures such as tractor trailer refrigerated truck enclosures wherein a smaller portable oxygen generator is thus used in conjunction with an $O_3$ generator and includes distribution fans for circulating the generated $O_3$ throughout the environment.

In some controlled environments where vegetables are stored for months at a time without ever opening the enclosure, the enclosure itself is sealed completely. The enclosure may contain its own fans for movement of the ambient gases contained therein over these long periods of time. With such fans already in place, the present invention can be used with $O_3$ injectors that are in fluid communication with the interior of the enclosed space to provide a controlled timed amount of $O_3$ and oxygen into the volume as a function of the empirical calculations to maintain a particular level of $O_3$ throughout the enclosure over a long period of time.

For use with enclosures that are not sealed for a long period of time and that do not have their own internal fans, the system includes the oxygen source, the ozone generator, and ozone gas nozzles strategically disposed relative to one or more fans and gas distribution housings to allow directionality when the unit is attached to a wall or ceiling in fluid communication with the enclosure ambient space. In this situation the flow of $O_3$ may be subject to a timer where the oxygen and ozone are periodically interjected into the enclosure through the fan housing in desired directions to keep a constant uniform mixture of $O_3$, oxygen and the gas in the ambient environment for the preservation of fruits and vegetables. Different types of vegetables such as onions or apples may give off different amounts of gases over a period of time that should be counteracted by the ozone environment.

In treating live animals such as swine that are maintained in an enclosure, ventilation takes on different aspects inasmuch as there is an oxygen and carbon dioxide transfer from the animals in addition to the other types of bacteria and fungus that may reside. Animals such as cows also give off large amounts of gases such as methene. In this environment, the system is used in conjunction with the overall ventilation system and may include numerous distribution fans that have $O_3$ injectors that remin on continuously in order to ensure the proper transfer of $O_3$ and distribution of ozone into the ambient atmosphere surrounding the animals. It is very important that the proper amount be maintained since too much ozone can hurt the animals.

With respect to the method aspects of the invention, the method of the invention involves first determining the amount of ozone necessary to properly sterilize a particular ambient atmosphere in an enclosure through empirical determination. The next step involves mounting an oxygen source for dry pure oxygen near the enclosure. The oxygen source has an outlet that supplies oxygen to an ozone generator that is a fixed adjacent or at least in fluid communication with the enclosure ambient atmosphere. Ozone is then periodically or continuously injected into the enclosed space in predetermined amounts as determined empirically to provide proper treatment for the objectives such as preserving a shelf life of particular vegetables enclosed or for reducing toxins in an animal confinement area. The ozone in certain embodiments is also distributed in predetermined patterns through the use of a gas transfer device such as fans that receive the ozone for maximum mixing affect in the ambient environment.

The system and method described herein provides a means for introducing and widely dispersing a high purity ozone mixed with a high purity oxygen within the storage environment. Because a single building may be a fixed base operation having separate refrigerated rooms of various sizes containing a variety of products, or in the case of a transport container must be self-contained, the system herein can be modular or totally self-contained. In the case of a fixed base or modular system, each module (ozone generator) is mounted directly in the storage room, or directly outside the storage room, with a means of injecting ozone into the closed room. This system can be configured to produce a variable quantity of ozone suited to the particular needs of the area being treated. Where the units are mounted in the storage room, each ozone generator has a sealed compartment containing the electronics where the ozone is generated, and an upper, open compartment containing a plurality of dispersing fans. The dispersing fans are mounted on mounting ports, wherein alternate mounting ports are also located in the upper compartment so that the dispersing fans can be relocated to any other mounting port in the upper compartment so that ozone can be directed in whatever direction provides the optimum pattern of dispersal. All components are corrosion resistant in consideration of the humid environment.

In the event the ozone generator must be mounted outside the storage room, as in the case of controlled atmosphere storage where the low oxygen level means the room cannot be opened in the event the ozone generator requires service, the unit only has the sealed compartment containing the electronics. The fans are eliminated from the upper compartment, and the ozone is piped directly into the storage room via a small diameter tube passing through the insulated wall of the storage room. The ozone is then dispersed by fans contained within the storage room.

In the preferred embodiment, the ozone generator modules are supplied with 85% to 92% purity oxygen from a centrally located oxygen concentrator. However, any source of dry, high purity oxygen will satisfy the requirements of the instant invention. As has been previously discussed, ambient air is not a suitable feed gas for the production of high purity ozone. This oxygen concentrating device concentrates the oxygen found in ambient air drawn from a clean or outside air source and eliminates most of the nitrogen and moisture. This oxygen is transported under low pressure (5 psig) to the various modules via a network of pipes. It is this concentrated dry oxygen that permits the ozone generator modules to produce such a high and consistent output of ozone in an adverse environment. The residual oxygen not converted to ozone is also introduced into the room where it also contributes at a lower level of chemical activity to the oxidation of ethylene gas.

The unit used in a transport container is essentially the same as the modular system described above, except that all the components, including the oxygen concentrator, are packaged in one very compact device which is generally small enough and light enough to be contained in the refrigeration compartment itself. Where the refrigeration compartment is too small, the unit can be mounted on an interior wall of the refrigeration compartment while displacing a very small portion of the cargo. The operation and affect is the same as the modular system described herein.

Animals confined in areas with high toxic gas levels exhibit symptoms of morbidity. Generally, extremities such as ears, lips, tongue and the hairless skin of newborn animals will lack the normal pink coloration. Extreme cases will have a grey coloration of the extremities. This is coupled with a lack of activity, reduced feeding and lack of weight gain. The animals are suffering from toxic gas poisoning which reduces the amount of oxygen dissolved in the blood stream which results in the lack of healthy coloration.

The introduction of a high purity oxygen and ozone mixture into the animal confinement room reduces the toxic gas levels by reaction with the ammonia and hydrogen sulphide. The ammonia is broken down into water vapor and free nitrogen. The hydrogen sulphide is broken down into water vapor and sulfur dioxide which is also a mild sterilant. By retaining a residual amount of ozone of 0.02 to 0.04 parts million by weight in the air in the room after available ozone is consumed by reaction with the gases, the bacteria and fungus in the air and on surfaces are continuously suppressed. Additionally, the animals airways (throat and lungs) are sterilized to a point that research indicates that viral infectious sights are reduced and mortality can be reduced.

The system and method described herein also provide a means of introducing and widely dispersing a high purity ozone mixed with a high purity oxygen within the animal confinement area. As described above, a single building may have separate rooms of various sizes containing a variable number of animals of various ages; therefore the animal confinement system is a modular one. Each module (ozone generator) is mounted directly in the room and can be configured to produce a variable quantity of ozone suited to the particular needs of the area being treated. Each ozone generator has a sealed compartment containing the electronics where the ozone is generated and an upper, open compartment containing a plurality of dispersion fans. The dispersion fans can be relocated to any of six other mounting ports in the upper cabinet so that ozone can be directed in whatever direction provides the optimum pattern of dispersion. This system provides thirteen different combinations of fan position. All components are corrosion resistant in consideration of the extreme environment.

The ozone generator models of the animal confinement system are supplied with 85%–92% purity oxygen from an oxygen source such as centrally located oxygen concentrator. The ambient air in the confinement rooms is such that it cannot be used to produce ozone directly without ultimate destruction of the high voltage ozone generator section. Nor can this atmosphere be used for the generation of concentrated oxygen due to the high concentration of corrosive gases. This oxygen concentrating device concentrates the oxygen found in ambient air drawn from a clean or outside air source and eliminates most of the nitrogen and moisture. This oxygen is transported under low pressure (5 psig) to the various modules via a network of pipes. It is this concentrated dry oxygen that permits the ozone generator modules to produce such a high output of ozone in a very adverse environment. The residual oxygen not converted to ozone is also introduced into the room where it also contributes at a lower level of chemical activity to the oxidation of toxic gases. Also, this residual oxygen contributes to a increase in the overall available oxygen in the animal confinement room.

It is an object of this invention to provide a method and apparatus for introducing high concentrations of ozone into a harvested fruit, vegetable, and flower storage or transport environment, as well as an animal confinement room.

Another object of this invention is to provide a method and apparatus for introducing high purity oxygen into a harvested fruit, vegetable, and flower storage or transport environment, as well as an animal confinement room.

Still another object of this invention is to provide a method and apparatus for dispersing ozone into the atmosphere of a storage environment by a fan or fans that can be quickly relocated within the body of the subject product such that ozone can be directed at the point of most need.

Still another object of this invention is to provide a method of distributing oxygen from a central location to a large number of individual ozone generators such that the adverse environment of the storage environment is not introduced into the oxygen concentrator nor the ozone generator.

And yet another object of this invention is to provide a method and apparatus whereby pathogens in the air, on surfaces, and in animal airways are suppressed with little or no use of chemicals, disinfectants, or pharmaceuticals.

And yet another object of this invention is to provide a method for reducing or eliminating the ethylene gas that accelerates the ripening of plant products and reduces the acceptable storage term of the products.

And yet another object of this invention is to provide a method and apparatus for introducing very high levels of ozone into an empty storage or transport environment for the purpose of deodorizing, sterilizing, and decontaminating prior to the introduction of product to be stored or transported.

And yet another object of this invention is to provide a method and apparatus for controlling the amount of ozone introduced into the storage or transport environment such that residual amounts of ozone do not exceed the limits for human exposure established by regulatory authorities.

And yet another object of this invention is to provide a method and apparatus whereby the health of the animals is improved without the introduction of increased amounts of outside air during times when to do so would either greatly increase the energy cost of heating or cooling introduced fresh air, or where the introduction of outside air might compromise the health of animals susceptible to chilling, drafts, or heat stress.

And yet another object of this invention is to provide a method and apparatus for introducing an area sterilant around the clock in an automatic fashion such that it reduces or eliminates the need for the manual application of disinfectants to the surfaces within the confinement area.

And yet still another object of the present invention is to provide a method and apparatus for reducing the levels of ammonia and hydrogen sulphide to which workers and animals in the confinement area are exposed.

In accordance with these and other objects which will become apparent hereinafter, the instant invention will now be described with particular reference to the accompanying drawings.

DESCRIPTION OF THE PREFERRED EMBODIMENTS

Figure 1:
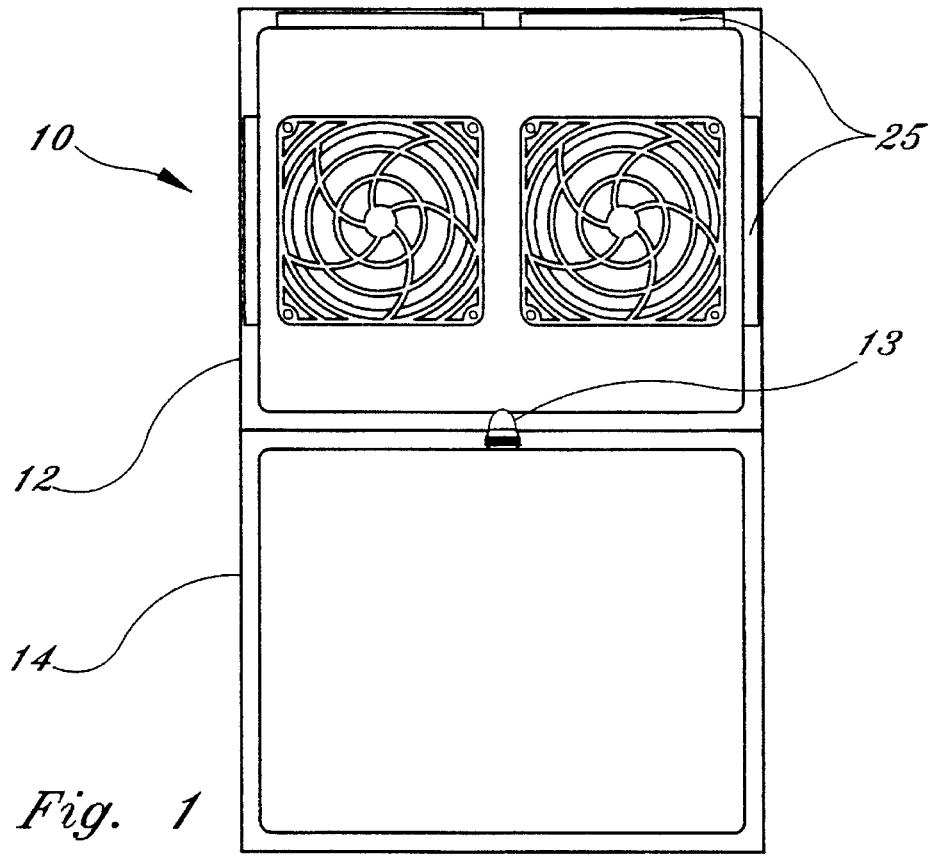
FIG. 1 is a front elevational view of one embodiment of the ozone generation unit of the instant invention.

With reference to the drawings, FIGS. 1–6 depict an apparatus for injecting and controlling the ambient gas in an enclosed space, generally indicated by the reference numeral 10. The system employs the use of the enclosed space (52a–52b; 62a–62b), a source of pure dry oxygen 40, an ozone generator 18, and a fluid transport communication system for transferring the ozone so generated into the desired enclosed space at desired levels for maintaining the ambient atmosphere in the enclosed space with desired levels of ozone and oxygen, depending on the ultimate purpose of the enclosed space.

Figure 2:
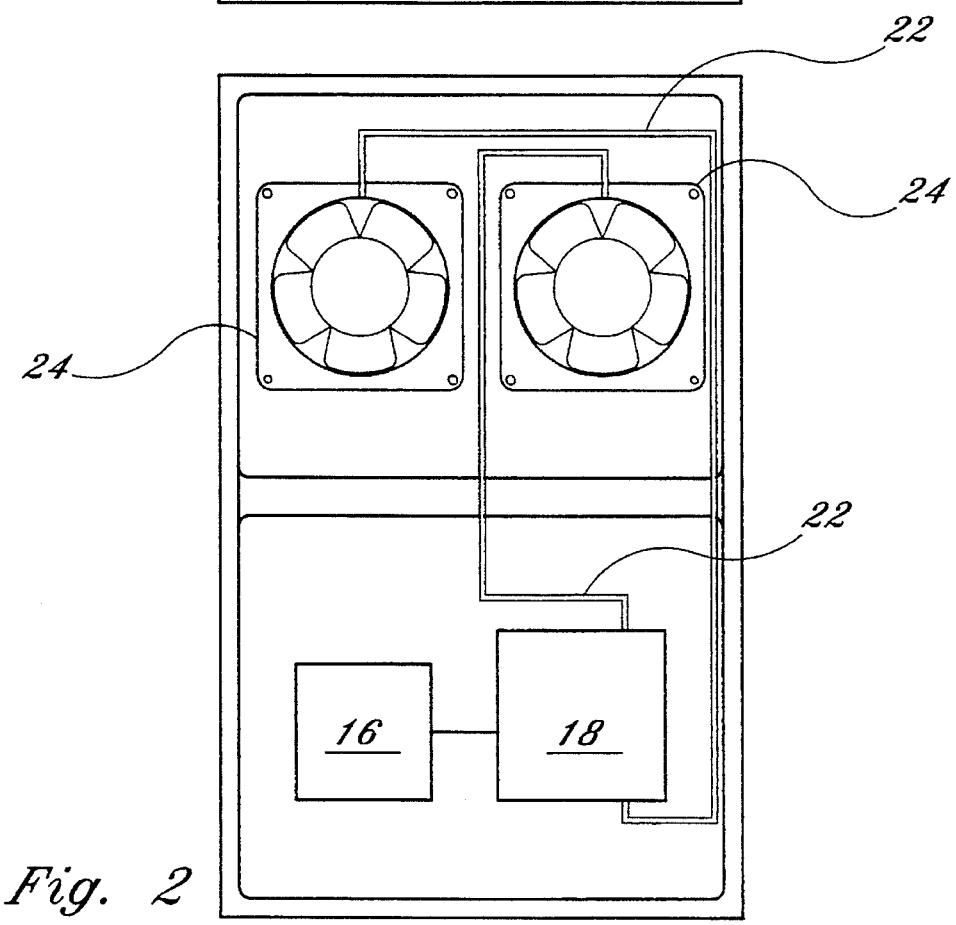
FIG. 2 is a rear elevational view of the ozone generation unit of FIG. 1, showing the connection between the upper and lower compartments.
Figure 3:
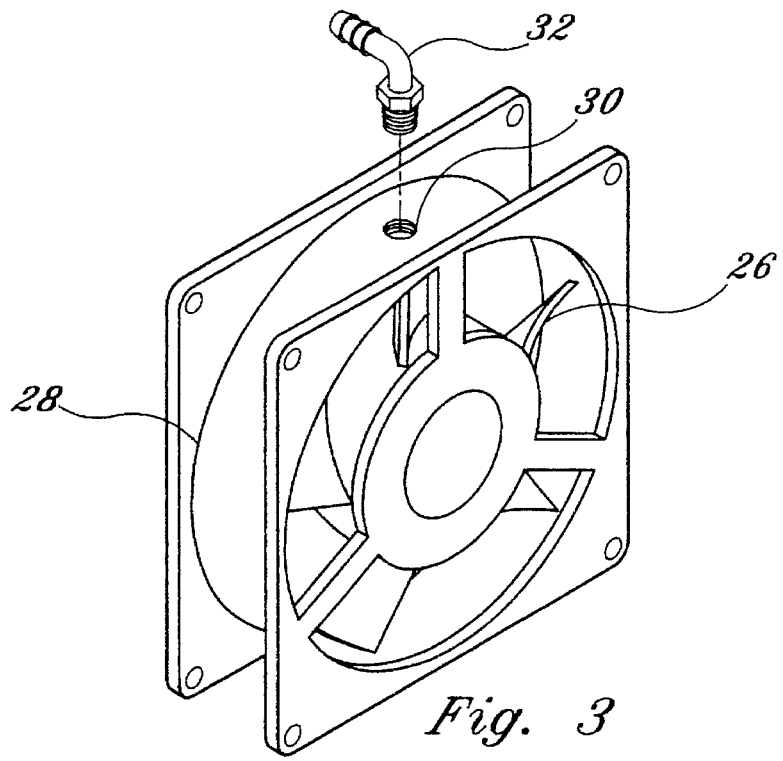
FIG. 3 is an exploded isometric view showing the fan assembly of the instant invention.
Figure 4:
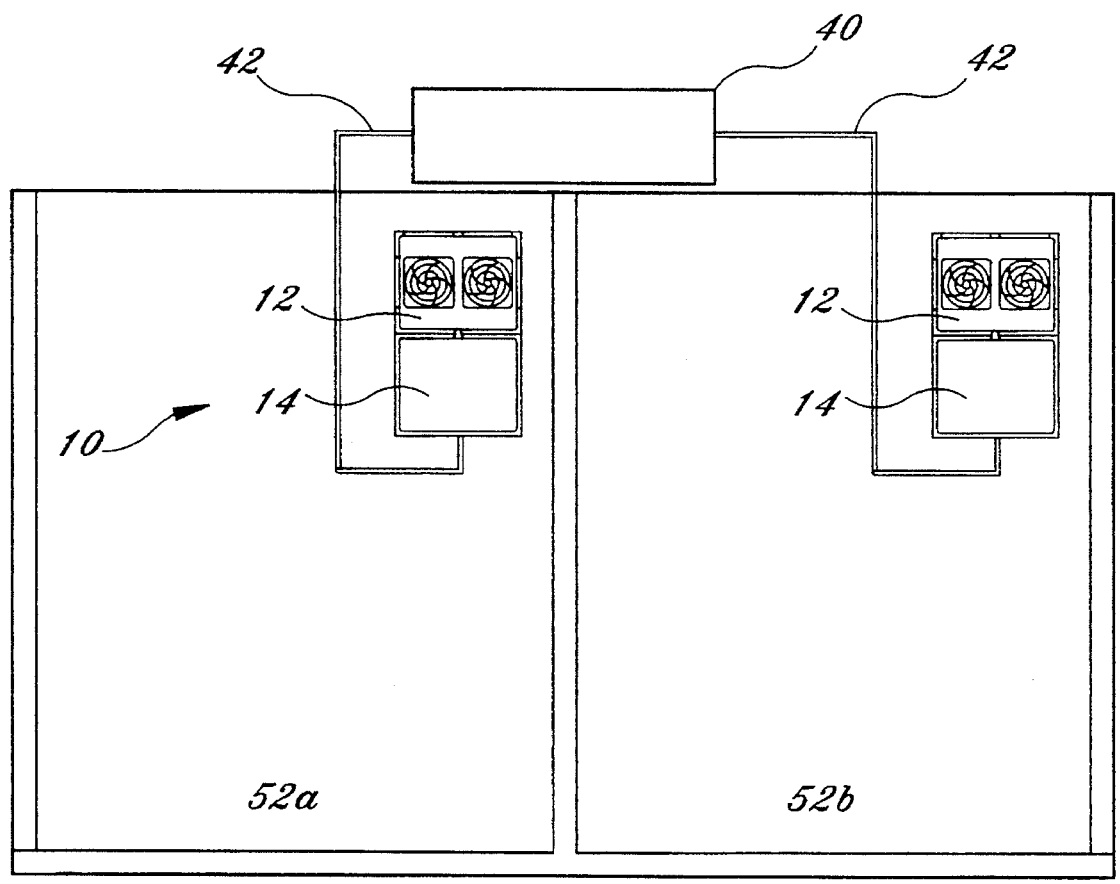
FIG. 4 is a pictorial view of the system of the instant invention.

Referring to FIGS. 1–6, oxygen source 40 may be an oxygen concentrator that has a fixed position relative to one or more rooms (52a–52b; 62a–62b), which are the enclosed spaces. As seen in FIG. 4, fluid control line 42 is disseminated from oxygen source 40 to a plurality of apparatuses 10 which are mounted on the back wall of enclosed spaces 52a–52b. Apparatuses 10 may also be mounted on any of the walls of the enclosed spaces, or on the ceiling. Referring back to FIGS. 1–6, the ozone generator 18 has a distribution device attached to its output, such as a system of fan assemblies 24, or a regulated pressure nozzle 20, or both, that allows for a predetermined amount of ozone to be distributed into each enclosed space as a function of time.

As seen in FIGS. 1 and 2, the unit 10 comprises an upper compartment 12 and a lower compartment 14, wherein LED power light 13 is electrically connected to lower compartment 14. Referring to FIG. 2, ozone generator 18 and transformer 16 are electrically connected, and are disposed within lower compartment 14. Ozone generator 18 is connected to at least one fan assembly 24 via conduit 22. As seen in FIGS. 1 and 2, fan assemblies 24 are mounted in upper compartment 12. The fan assemblies 24 are mounted on mounting ports, wherein alternate mounting ports 25 are also located in the upper compartment 12 so that the fan assemblies 24 can be relocated to any other mounting port in the upper compartment 12, so that ozone can be directed in whatever direction provides the optimum pattern of dispersal for the particular enclosed space.

Referring now to FIG. 3, a fan assembly is shown, comprising fan blades 26, fan housing 28, and threaded aperture 30 disposed in the top surface of fan housing 28. Aperture 30 is disposed in the top surface of fan housing 28, such that aperture 30 is centered in the swept area. Fitting 32, in the form of an elbow and nozzle, is screwed into threaded aperture 30 at the upper periphery of the fan housing, and in such close proximity (e.g. 0.002" to 0.010") to the outer tip of the fan blades 26, such that crystalline products of oxidation which constantly accumulate at the point where the highest concentration of oxidizer meets the room air are removed by the suction and pulsating action of the passing fan blades 26. In a typical installation, fan assembly 24 has five blades and operates at from 2,900–3,200 revolutions per minute. This results in 14,500–16,000 pulsations per minute, which keeps the injector orifice clear of debris and keeps the injection point clear of solidified products of oxidation that might otherwise block the injector tube. Furthermore, in an animal confinement environment, dust from animal feed and dry feces, and animal hair, which accumulate on and around the fan, do not dislodge and fall into the small injection orifice because it is at the top of the fan. This action keeps the injection point clear of debris that might otherwise block the injection tube.

Figure 5:
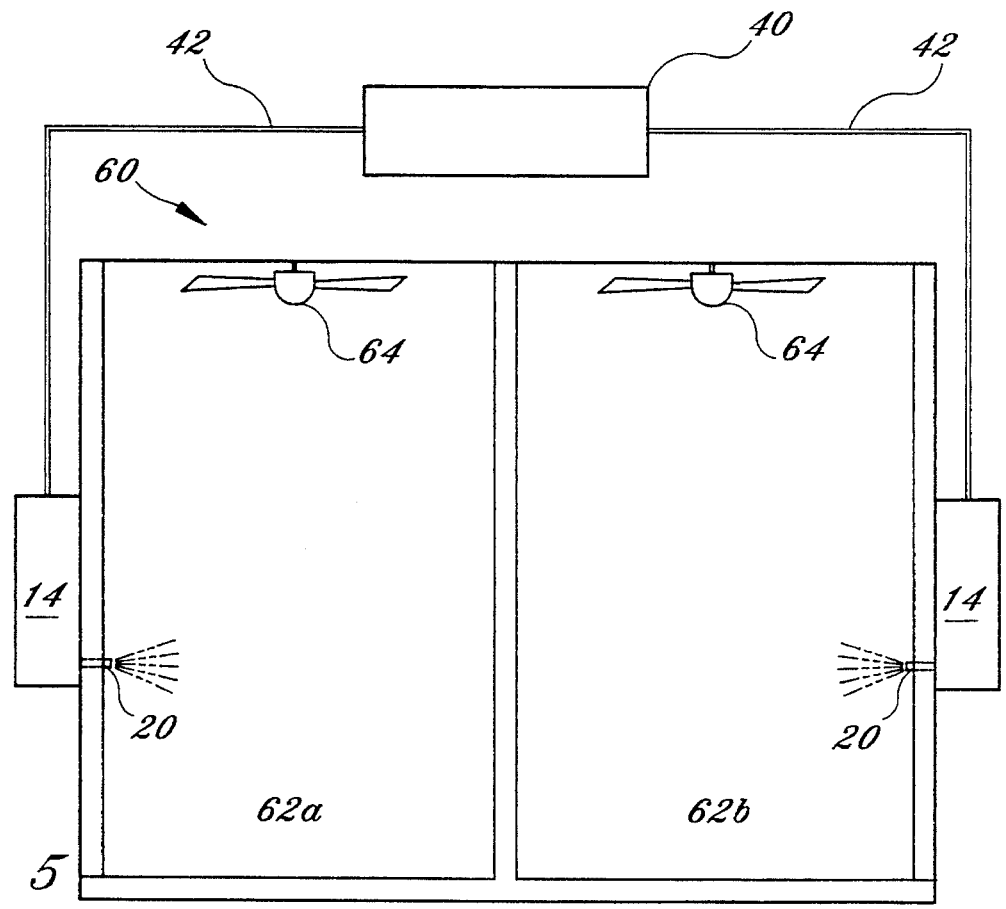
FIG. 5 is a pictorial view of an alternate embodiment of the system of the instant invention.

Referring now to FIG. 5, an alternate embodiment of the instant invention is shown, wherein vegetables are stored for months at a time without ever opening the enclosure. In this embodiment, the enclosure itself is sealed completely. The enclosure (62a, 62b) may contain its own fans 64 for movement of the ambient gases contained therein over these long periods of time. With such fans already in place, the present invention can be used with $O_3$ injectors 20 that are in fluid communication with the interior of the enclosed space (62a, 62b) to provide a controlled, timed amount of ozone and oxygen into the volume as a function of the empirical calculations to maintain a particular level of $O_3$. In this embodiment, the unit 10 is mounted outside the storage room or enclosed area 62a, 62b, and the unit 10 only has the lower compartment 14 containing the ozone generator and transformer. The fans are eliminated from the upper compartment 12, and the ozone is piped directly into the storage room 62a, 62b via a small diameter tube 22, passing through the insulated wall of the storage room or enclosed area. The ozone is then dispersed by fans 64 contained within the storage room. As described above, the ozone generator modules 18 are supplied with 85%–92% purity oxygen from a centrally located oxygen source 40.

Figure 6:
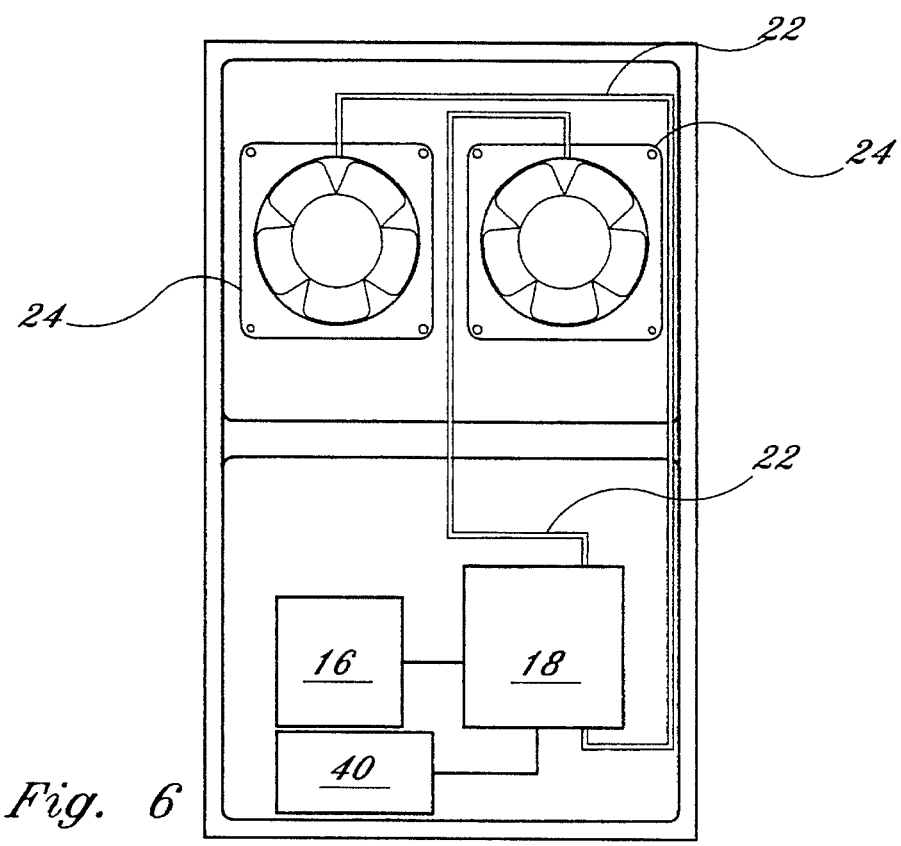
FIG. 6 is a rear elevational view of an alternate embodiment of the ozone generation unit for use in a transport container.

Referring now to FIG. 6, another alternate embodiment of the instant invention is shown for use in a transport container. The unit used in a transport container is essentially the same as the modular system described above, except that all the components, including the oxygen source 40, are packaged in one very compact device, which is generally small enough and light enough to be contained in the refrigeration compartment itself.

The system and method described herein provides a means of introducing and widely dispersing a high purity ozone mixed with a high purity oxygen within an enclosed area. Each unit has a sealed compartment 14 containing the electronics where the ozone is generated. In the preferred embodiment, the unit has a sealed compartment containing the electronics where the ozone is generated and an upper, open compartment containing a plurality of dispersion fans. The dispersion fans can be relocated to any of six other mounting ports in the upper compartment so that ozone can be directed in whatever direction provides the optimum pattern of dispersion.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A system for disinfecting an enclosed space, said system having an output in fluid communication with the enclosed space, said system comprising:

an enclosed space;

a source of high purity oxygen;

ozone generation means for generating ozone connected to said high purity oxygen source, said ozone generation means converting the high purity oxygen into a high purity oxygen and ozone mixture, said ozone generation means having at least one output;

at least one ozone distribution device including a dispersion fan for dispersing the high purity oxygen and ozone mixture into the enclosed space, said at least one dispersion fan connected to an output of said ozone generation means, said at least one dispersion fan disposed in a housing having a top surface, said housing top surface having an aperture disposed downwardly therein, said dispersion fan further comprising a nozzle disposed within said top surface aperture, such that the ozone and oxygen mixture is injected at the upper periphery of the dispersion fan within 0.01 inches of the outer tip of the fan blades whereby said fan blades revolve at a rate such that 14,500–16,000 pulsations per minute are generated by the rotation of said fan blades thereby preventing the accumulation of solidified products of oxidation and the accumulation of debris from within the enclosed space from clogging said nozzle; and means for controlling said ozone generating means in response to the concentration of ozone within the enclosed space, thereby maintaining a predetermined ozone concentration within said enclosed space.

2. A system as recited in claim 1, wherein said high purity oxygen is between 85%–92% purity.

3. A system for disinfecting an enclosed space according to claim 1, wherein said distribution device includes at least one unit located within said enclosed space, said unit housing said at least one fan and having a plurality of fan mounting ports such that said at least one fan can be selectively positioned within one of said fan mounting ports for uniform dispersal of said mixture.

* * * * *